United States Patent
Stadnicki

(10) Patent No.: US 8,778,692 B2
(45) Date of Patent: Jul. 15, 2014

(54) MEASUREMENT METHOD FOR MEASURING THE LEVEL OF HALOGEN AGENTS IN SWIMMING-POOL WATER

(75) Inventor: Zbigniew Stadnicki, Cales (FR)

(73) Assignee: Pacific Industrie, Boulaxac (FR)

( * ) Notice: Subject to any disclaimer, the term of this patent is extended or adjusted under 35 U.S.C. 154(b) by 523 days.

(21) Appl. No.: 13/128,359

(22) PCT Filed: Nov. 17, 2009

(86) PCT No.: PCT/FR2009/001323
§ 371 (c)(1),
(2), (4) Date: May 9, 2011

(87) PCT Pub. No.: WO2010/055236
PCT Pub. Date: May 20, 2010

(65) Prior Publication Data
US 2011/0217788 A1    Sep. 8, 2011

(30) Foreign Application Priority Data
Nov. 17, 2008   (FR) ...................................... 08 06409

(51) Int. Cl.
*G01N 33/18*    (2006.01)
(52) U.S. Cl.
USPC ............... 436/125; 436/34; 436/51; 436/124; 436/164
(58) Field of Classification Search
USPC .............................. 436/34, 51, 124–125, 164
See application file for complete search history.

(56) References Cited

U.S. PATENT DOCUMENTS

| | | | |
|---|---|---|---|
| 1,960,615 A * | 5/1934 | Baker | 137/93 |
| 1,986,403 A * | 1/1935 | Lehmkuhl | 436/125 |
| 2,977,199 A | 3/1961 | Quittner | |
| 3,226,195 A | 12/1965 | De Lisle Nichols et al. | |
| 3,466,450 A | 9/1969 | Goodman et al. | |
| 3,574,553 A | 4/1971 | Herbert et al. | |
| 3,915,644 A * | 10/1975 | Walraven | 436/34 |
| 4,207,450 A | 6/1980 | Mittleman | |
| 4,399,101 A * | 8/1983 | Queen | 422/82.09 |
| 4,865,992 A * | 9/1989 | Hach et al. | 436/51 |
| 5,004,696 A * | 4/1991 | Clinkenbeard | 436/51 |
| 5,098,186 A * | 3/1992 | Bull | 356/246 |
| 5,284,770 A * | 2/1994 | Adrian et al. | 436/8 |
| 6,180,412 B1 | 1/2001 | Kroll | |
| 6,881,583 B2 * | 4/2005 | Kahle | 436/113 |
| 2003/0232447 A1 * | 12/2003 | Kahle | 436/113 |

FOREIGN PATENT DOCUMENTS

CA          2169248 A1    8/1997

* cited by examiner

*Primary Examiner* — Arlen Soderquist
(74) *Attorney, Agent, or Firm* — Sughrue Mion, PLLC

(57) ABSTRACT

The invention relates to a method of monitoring a concentration of a halogenated disinfectant in swimming pools or the like and a device for implementing the method. The method comprises: a liquid-injection step of injecting the liquid to be analyzed into the analysis chamber; a reagent-injection step of injecting a reagent into the analysis chamber; a measurement step of measuring the liquid/reagent mixture by colorimetry; a processing step of processing the measurement in relation to data; and a verification step of verifying the colorimetric measurement when the measurement corresponds to the reagent being bleached or to an absence of reaction color.

8 Claims, 1 Drawing Sheet

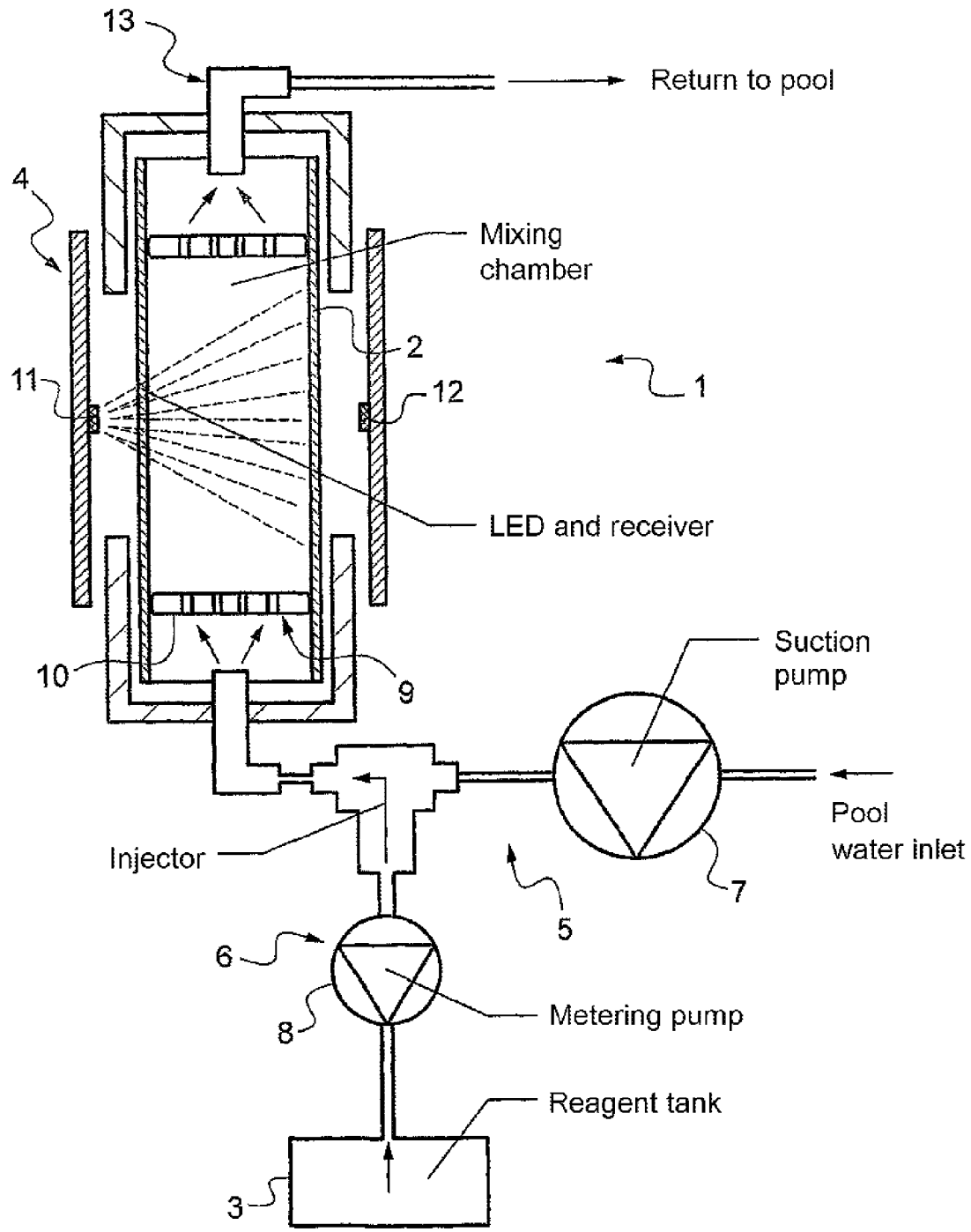

MEASUREMENT METHOD FOR MEASURING THE LEVEL OF HALOGEN AGENTS IN SWIMMING-POOL WATER

CROSS REFERENCE TO RELATED APPLICATIONS

This application is a National Stage of International Application No. PCT/FR2009/001323 filed Nov. 17, 2009, claiming priority based on French Patent Application No. 08 06409 filed Nov. 17, 2008, the contents of all of which are incorporated herein by reference in their entirety.

The present invention relates to a method and device for monitoring a concentration of a halogenated disinfectant in a swimming pool or the like.

The invention finds advantageous application in the field of monitoring the concentration of chlorine or bromine in private swimming pools, in particular outdoor swimming pools.

However, although particularly designed for such an application, the method and device could be used for monitoring and processing water in public pools, or in various types of pools, in particular Jacuzzis or aquariums.

BACKGROUND OF THE INVENTION

Outdoor swimming pools are being associated more and more frequently with protective covers and/or shelters. These elements make it possible to keep the pool clean by reducing dirt and grime from the outside, and they also contribute to making swimming pools safer, shelters having the added advantage of increasing the duration of the bathing season.

Conventionally, covers and the transparent surfaces of shelters are treated so as to filter out ultraviolet rays. The Applicant has found that variation in the amount of ultraviolet rays reaching the water of a swimming pool strongly influences the rate at which halogens such as chlorine and bromine disappear.

As a general rule, doses of chlorine or bromine are calculated depending on the characteristics of the swimming pool when said swimming pool is not covered. When the swimming pool is covered, the rate at which the chlorine and bromine disappear is considerably slowed down and consequently, due to lack of regulation in real time, the concentration increases rapidly and becomes too high. That concentration that is too high is detrimental because it makes the water aggressive to the skin and to the liner of the pool. Another drawback is that the lack of regulation leads to too much disinfectant being consumed.

A regulating device is available on the market for measuring, in real time, the concentration of halogenated disinfectant. However, that device uses a probe based on the redox effect and is not satisfactory. Measurement of redox potential is not reliable in view of many external factors interfering with such measurements. Moreover, the device deduces that chlorine or bromine are absent if there is no electrolysis, yet such absence of electrolysis may be due to a low microbe presence in the water being analyzed. In that event, the device causes a new dose of disinfectant to be added, even though the concentration of disinfectant may be greater than the required maximum concentration.

A device has also been proposed for measuring concentrations of chlorine, in real time, by using a reagent that reacts in the presence of chlorine, said reagent being associated with a colorimetric detector. However, that device is not reliable in the sense that the reagent is bleached when the concentration of chlorine exceeds a certain limit, thus distorting the measurement. In contrast, the device is unable to distinguish between an absence of reagent in the mixture and a concentration of chlorine that is low, and therefore it can cause chlorine to be added when the concentration of chlorine is sufficient or even greater than the required maximum concentration.

OBJECT OF THE INVENTION

The present invention aims to provide a method and device for measuring the concentration of halogenated disinfectant in real time, without the risk of a false measurement due to phenomena of bleaching or due to a lack of reagent injection.

SUMMARY OF THE INVENTION

To this end, the monitoring method comprises:
- a liquid-injection step of injecting the liquid to be analyzed into the analysis chamber;
- a reagent-injection step of injecting a colored reagent into the analysis chamber;
- a measurement step of measuring the liquid/reagent mixture by colorimetry;
- a processing step of processing the measurement in relation to data; and
- a verification step of verifying the colorimetric measurement when the measurement corresponds to the reagent being bleached or to an absence of reaction color.

In the event of suspect measurements being detected during the processing step, this verification step makes it possible to detect a high concentration of halogenated compounds giving rise to bleaching, or indeed to detect a problem of reagent supply in the analysis chamber. This verification step is advantageously followed by a command step, thus making it possible to have a suitable dose of disinfectant in real time.

The invention also relates to a device for implementing the above-mentioned method, the device comprising an analysis chamber, a reagent tank, colorimetric analysis means, and first and second introduction means respectively for introducing liquid to be analyzed and reagent into the chamber. The device also includes means for mixing the colored reagent with the water to be analyzed, said mixer means having at least one baffle.

BRIEF DESCRIPTION OF THE DRAWING

The present invention can be better understood on reading a detailed example of an embodiment with reference to the accompanying drawing, provided as a non-limiting example, diagrammatically showing an embodiment of the device of the invention.

DETAILED DESCRIPTION OF THE INVENTION

With reference to FIG. 1, a device 1 of the invention is shown with an analysis chamber 2, a reagent reservoir 3, and colorimetric analysis means 4.

The device 1 further comprises first introduction means 5 that are arranged between analysis chamber 2 and the inlet for the liquid to be analyzed, typically the water supply inlet of the swimming pool, and second introduction means 6 for introducing reagent into analysis chamber 2.

In the example of FIG. 1 these introduction means 5 and 6 share a three-port injector, however, in another embodiment, the reagent and the liquid are introduced independently.

In advantageous manner, the first introduction means 5 comprise a peristaltic pump 7. However, in a variant embodiment provision is made for the water not to be introduced by a pump but rather by a system generating a pressure difference. The second introduction means 6 comprise a metering pump 8 for injecting precise volumes of reagent into analysis chamber 2.

In order to homogenize the mixture of the liquid to be analyzed and the reagent, mixer means 9 are provided at the inlet to the analysis chamber 2. Advantageously, said mixer means 9 are stationary and consist of baffles 10 or deflectors that perform stirring that facilitates mixing. However, in a variant embodiment, the mixer means 9 consist of movable equipment such as motor-driven propellers.

Colorimetric analysis is carried out in the analysis chamber 2 by colorimetric analysis means 4 comprising a set of light-emitting diodes (LEDs) 11 associated with receivers 12 and with processing means (not shown in the accompanying FIGURE).

Advantageously, at the outlet of the analysis chamber 2, provision is made for filter means 13, and filtered liquid is returned into the swimming pool system. However, in another embodiment, given the small volumes that are analyzed, provision is made merely for a recovery tank for recovering the mixture, said mixture being treated or recycled in a separate device.

The monitoring method is described as a function of the device 1 that is presented above and that is particularly suited to said method, however it is important to note that the method could be implemented in other devices.

In a first step, the first introduction means 5 are controlled to inject liquid to be analyzed into the analysis chamber 2. This step may be initiated at fixed or variable intervals according to a determined program.

The method further includes injecting a colored reagent into the analysis chamber 2. The injection may be performed one or more times, with durations and injection volumes that are variable. Advantageously, in the colorimetric measurement step prior to the processing step, a single injection is performed so as to limit the amount of reagent that is consumed.

The method then consists in processing the colorimetric measurement of the mixture in a step of processing stored data. In a preferred embodiment, and in order to perform analysis that is reliable, a plurality of measurements are performed in order to obtain a statistical value. This value is then compared to stored data corresponding to reference values and/or historical values.

When this value is statistically consistent with the reference values and/or historical values, the analysis is finished. The statistical value serves as the basis for causing an electrolyzer or a chlorine pump to operate when the analyzed chlorine level is too low. The device then goes on standby until the next analysis.

When the colorimetric measurement or the statistical value corresponds to measuring bleaching of the reagent or to an absence of reaction color, the method includes a verification step.

This verification step depends on the measurement taken in the previous step if that measurement corresponds to bleaching of the reagent, which occurs when the concentration of halogenated compound exceeds a limit, the verification step consists in injecting at least one more dose of reagent and in performing a series of colorimetric readings during the stages of injecting and mixing the colored reagent with the liquid to be analyzed. These various measurements are used to calculate the rate at which colored reagent is absorbed and to confirm that the reagent is being bleached.

If the concentration of halogenated compound is high, then bleaching is very fast for a low dose of reagent, and therefore it is impossible to determine a reaction rate reliably. When the measurements obtained during an injection do not enable a conclusion to be drawn with any certainty about whether bleaching is taking place or a measurement error occurred in the measurement step carried out at the beginning of the method, then the verification step comprises repeated injection steps, at determined intervals, using increasing doses of reagent. When the dose is large enough to determine a reaction rate, the processing means serve to identify bleaching and the concentration of halogenated compound as a function both of the reaction rate and of the volume of reagent injected into the analysis chamber.

When the measurement or statistical value obtained by the colorimetric measurement and processing steps corresponds to an absence of reaction color, the verification step consists in injecting at least one more dose of reagent and in measuring brightness in the analysis chamber 2 in order to distinguish too low a concentration of halogenated compound from a failure to inject any colored reagent. By ordering at least one additional dose of reagent to be injected, if the device does actually send reagent into the analysis chamber, then an increase is obtained in the concentration of colored reagent that results in a change in brightness, the reagent being colored. Advantageously, in order to study the changes in brightness precisely, the verification step includes injecting doses of colored reagent with increasing durations. If the reagent is not sent into analysis chamber, brightness measurements vary little or not at all over time, and consequently the method makes it possible to distinguish between an absence of reaction that is due to a concentration of halogenated compound that is very low or zero, or that is due to a failure in the reagent introducing means or a lack of reagent in the reservoir.

The method therefore makes it possible to avoid causing disinfectant to be dispensed into the swimming pool because of a misinterpretation of colorimetric measurements and also, in an advantageous embodiment, to have this taken into account by means of a device malfunction warning.

In advantageous manner, so as not to distort the measurements from one control cycle to the next, the method includes a step of rinsing the analysis chamber 2 at the end and/or at the beginning of each colorimetric measurement cycle.

According to an advantageous feature of the method, provision is also made for a step of filtering the mixture of liquid and colored reagent in order to reduce the residues due to monitoring of the liquid to be analyzed.

Naturally, other characteristics of the invention could also be envisaged without going beyond the ambit of the invention defined by the claims below.

What is claimed is:

1. A method of monitoring a concentration of a halogenated disinfectant in a swimming pool or the like, said method comprising:
    a liquid-injection step of injecting the liquid to be analyzed into the analysis chamber (2);
    a reagent-injection step of injecting a colored reagent into the analysis chamber (2);
    a measurement step of measuring the liquid/reagent mixture by colorimetry;
    a processing step of processing the measurement in relation to data; and
    a verification step of verifying the colorimetric measurement when the measurement corresponds to the reagent being bleached or to an absence of reaction color.

2. A monitoring method according to claim 1, wherein the verification step consists in injecting at least one more dose of reagent and in performing a series of colorimetric readings during the stages of injecting and mixing the colored reagent with the liquid to be analyzed in order to determine the rate at which the colored reagent is absorbed, thereby enabling bleaching of the reagent to be detected.

3. A monitoring method according to claim 2, wherein the verification step includes injecting increasing doses of colored reagent at determined intervals.

4. A monitoring method according to claim 1, wherein the verification step consists, in the absence of reaction color, in injecting at least one more dose of reagent and in measuring the brightness in the chamber in order to distinguish a concentration of chlorine that is too low from a failure to inject colored reagent.

5. A monitoring method according to claim 4, wherein the verification step includes injecting doses of colored reagent with increasing durations.

6. A monitoring method according to claim 1, wherein the method further comprises a step of ordering a dose of disinfectant to be sent.

7. A monitoring method according to claim 1, wherein the method further comprises a step of filtering the liquid and colored reagent mixture.

8. A monitoring method according to claim 1, wherein the method further comprises a step of rinsing the analysis chamber.

* * * * *